United States Patent [19]

Serban

[11] 3,930,837

[45] Jan. 6, 1976

[54] 3-CHLORO-5-ACETAMIDAISOQUINOLINE AS A HERBICIDE

[75] Inventor: Alexander Serban, Doncaster, Australia

[73] Assignee: ICI Australia Limited, Melbourne, Australia

[22] Filed: Dec. 14, 1972

[21] Appl. No.: 314,910

[30] Foreign Application Priority Data
Dec. 31, 1971  Australia............................ 7569/71
Aug. 28, 1972  Australia............................. 243/72

[52] U.S. Cl. ............. 71/94; 260/283 R; 260/283 S; 260/283 CN; 260/286 R; 260/288 R; 260/289 R; 424/258; 71/DIG. 1
[51] Int. Cl.$^2$................................................ A01N 9/22
[58] Field of Search................................ 71/94, 67

[56] References Cited
UNITED STATES PATENTS

| 2,661,276 | 12/1953 | Schlesinger et al. | 71/94 |
| 2,661,277 | 12/1953 | Mowry et al. | 71/94 |
| 2,665,203 | 1/1954 | Emerson | 71/94 |
| 2,692,822 | 10/1954 | Denny | 71/94 |
| 2,870,153 | 1/1959 | Heininger | 71/94 |
| 3,000,894 | 9/1961 | Bimber | 71/94 |
| 3,235,556 | 2/1966 | Wakeman | 71/67 |
| 3,247,212 | 4/1966 | Johnson | 71/94 |
| 3,277,096 | 10/1966 | Johnson | 71/94 |
| 3,285,923 | 11/1966 | Wakeman | 71/67 |

Primary Examiner—Glennon H. Hollrah
Attorney, Agent, or Firm—Cushman, Darby & Cushman

[57] ABSTRACT

Biologically active compositions of matter comprising substituted isoquinolines and salts thereof. Certain of the compounds and their salts are novel. Acaricidal, fungicidal, herbicidal and insecticidal activity is demonstrated. In particular 3-chloro-5-acetamidoisoquinoline shows good activity as a selective pre-emergence herbicide, and 4-bromo-5-nitro-isoquinoline shows good fungicidal activity against Erysiphe graminis (wheat powdery mildew).

3 Claims, No Drawings

3-CHLORO-5-ACETAMIDAISOQUINOLINE AS A HERBICIDE

This invention relates to organic compounds having biological activity and in particular to organic compounds exhibiting herbicidal, insecticidal, acaricidal or fungicidal activity, to compositions containing them, to processes for controlling undesired vegetation and fungi, and to processes for eradicating undesired insects, mites and ticks.

We have found that certain substituted isoquinoline compounds and their salts exhibit biological activity, particularly herbicidal, insecticidal, acaricidal and fungicidal activity.

According to the present invention we provide biologically active compositions exhibiting herbicidal, insecticidal, acaricidal, and fungicidal activity, said compositions comprising as active ingredient at least one substituted isoquinoline compound of formula:

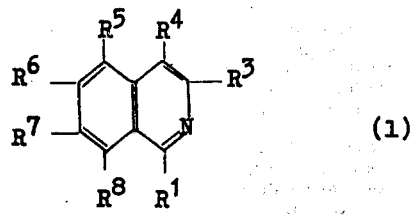

wherein each of $R^1$, $R^3$, $R^4$, $R^5$, $R^6$, $R^7$ and $R^8$, which may be the same or different, is selected from the group consisting of hydrogen, alkyl, halo, nitro, amino, mono- and di-alkyl substituted amino, mono- and di-aryl substituted amino, acyl substituted amino, cyano, arylthio, alkylthio, and alkoxy, with the proviso that if $R^3$ is amino or substituted amino, then $R^1$ may not be halogen, alkylthio, or arylthio.

We also provide biologically active compositions exhibiting herbicidal, insecticidal, acaricidal, or fungicidal activity, said compositions comprising as active ingredient an isoquinoline salt of formula:

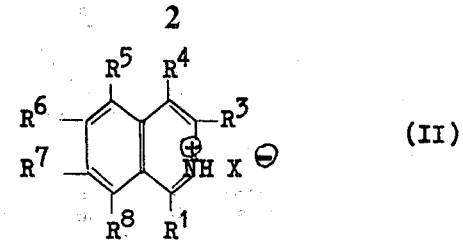

wherein $R^1$, $R^3$, $R^4$, $R^5$, $R^6$, $R^7$ and $R^8$ are as defined hereinabove and in addition, one or more of $R^1$, $R^3$, $R^4$, $R^5$, $R^6$, $R^7$ and $R^8$ may be the amine salt group having the formula:

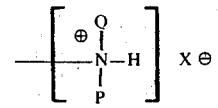

wherein P and Q are selected from the group consisting of hydrogen, alkyl, substituted alkyl, aryl, and substituted aryl; HX is any inorganic acid, organic acid, or acidic phenol capable of forming a salt with an isoquinoline compound of the general formula (I) hereinabove.

Preferably HX is selected from the group consisting of hydrogen halides, sulphuric acid, organic carboxylic acids capable of forming stable isoquinoline salts of general formula (II), and phenols substituted in at least one of the 2, 4 or 6 positions of the aromatic nucleus with a strongly electro-negative group, to render the phenols sufficiently acidic to form stable isoquinoline salts of general formula (II) hereinabove.

Most preferably HX is selected from the group of inorganic acids consisting of hydrogen fluoride, hydrogen chloride, hydrogen bromide, hydrogen bromide, hydrogen iodide and sulphuric acid; or from the group of organic carboxylic acids consisting of trifluoroacetic acid, trichloroacetic acid, monochloro-difluoro-acetic acid, α,α-dichloro-propionic acid, pentafluoropropionic acid, mono- or poly-nitro-substituted benzoic acid; or from the group of acidic phenols consisting of pentachlorophenol, tetrabromo-m-cresol, 2,6-dichloro-4-nitro-phenol, 2,6-dibromo-4-nitro-phenol, and 2,4-dinitrophenol.

Examples of typical compounds of the general formulae (I) and (II) are set out below in Table (I) wherein appropriate substituents for $R^1$, $R^3$ to $R^8$ inclusive and HX are indicated.

TABLE I

| $R^1$ | $R^3$ | $R^4$ | $R^5$ | $R^6$ | $R^7$ | $R^8$ | HX |
|---|---|---|---|---|---|---|---|
| H | methyl | H | H | H | H | H | — |
| H | methyl | H | nitro | H | H | H | — |
| n-butyl | H | H | H | H | H | H | — |
| H | methyl | H | amino | H | H | H | — |
| H | amino | H | H | H | H | H | — |
| chloro | chloro | H | H | H | H | H | — |
| bromo | bromo | H | H | H | H | H | — |
| H | chloro | H | H | H | H | H | — |
| H | bromo | H | H | H | H | H | — |
| chloro | chloro | H | nitro | H | H | H | — |
| chloro | chloro | H | amino | H | H | H | — |
| H | chloro | H | H | H | H | H | hydrogen chloride |
| H | H | H | H | H | H | H | hydrogen chloride |
| H | methyl | H | H | H | H | H | hydrogen chloride |
| H | methyl | H | nitro | H | H | H | hydrogen chloride |
| H | chloro | H | amino | H | H | H | — |
| H | chloro | H | nitro | H | H | H | — |
| H | chloro | H | chloro | H | H | H | — |
| H | H | H | nitro | H | H | H | — |
| H | H | H | nitro | H | H | H | hydrogen chloride |
| H | H | H | amino | H | H | H | — |
| H | H | H | H | H | H | H | — |
| H | H | H | fluoro | H | H | H | — |
| H | H | H | H | H | H | H | trifluoroacetic |

TABLE I-continued

| R¹ | R³ | R⁴ | R⁵ | R⁶ | R⁷ | R⁸ | HX |
|---|---|---|---|---|---|---|---|
| H | H | H | nitro | H | H | H | trifluoroacetic acid |
| H | methyl | H | nitro | H | H | H | hydrogen bromide |
| H | methyl | H | nitro | H | H | H | trifluoroacetic acid |
| H | methyl | H | nitro | H | H | H | hydrogen iodide |
| H | H | H | nitro | H | H | H | hydrogen iodide |
| H | H | H | H | H | H | H | hydrogen iodide |
| H | H | H | chloro | H | H | H | — |
| H | H | H | H | H | H | H | trichloroacetic acid |
| H | H | H | H | H | H | H | hydrogen bromide |
| H | H | H | bromo | H | H | H | — |
| H | H | H | bromo | H | H | H | hydrogen chloride |
| H | H | H | fluoro | H | H | H | hydrogen chloride |
| H | H | H | chloro | H | H | H | hydrogen chloride |
| H | chloro | H | fluoro | H | H | H | — |
| H | methyl | H | H | H | H | H | hydrogen iodide |
| methyl | H | H | H | H | H | H | hydrogen iodide |
| methyl | H | H | nitro | H | H | H | — |
| H | H | H | H | H | H | H | pentachlorophenol |
| bromo | H | H | nitro | H | H | H | — |
| H | H | H | chloro | H | H | nitro | — |
| H | H | H | nitro | H | H | H | 2,6-dibromo-4-nitro-phenol |
| H | H | H | nitro | H | H | H | tetrabromo-m-cresol |
| H | H | H | nitro | H | H | H | hydrogen bromide |
| methyl | H | H | nitro | H | H | H | trifluoroacetic acid |
| methyl | H | H | nitro | H | H | H | hydrogen iodide |
| butyl | H | H | nitro | H | H | H | hydrogen iodide |
| H | H | H | H | H | H | H | mono-chlorodifluoro-acetic acid |
| H | H | H | H | H | H | H | α,α-dichloro-propionic acid |
| H | H | H | nitro | H | H | H | mono-chlorodifluoro-acetic acid |
| H | H | H | nitro | H | H | H | pentafluoroprop-ionic acid |
| H | H | H | nitro | H | H | H | pentachlorophenol |
| methyl | H | H | H | H | H | H | — |
| H | H | H | nitro | H | H | H | 2,6-dichloro-4-nitrophenol |
| H | chloro | H | H | H | H | H | hydrogen iodide |
| H | chloro | H | H | H | H | H | hydrogen bromide |
| H | H | H | nitro | H | H | H | 2,4-dinitro-benzoic acid |
| H | methyl | H | H | H | H | nitro | hydrogen bromide |
| H | H | H | chloro | H | H | nitro | hydrogen bromide |
| H | H | H | nitro | H | H | H | 2,4-dinitrophenol |
| nitro | H | H | H | H | H | H | — |
| nitro | H | H | H | H | H | H | hydrogen chloride |
| nitro | H | H | H | H | H | H | trifluoroacetic acid |
| H | nitro | H | H | H | H | H | hydrogen chloride |
| H | nitro | H | H | H | H | H | — |
| H | nitro | H | H | H | H | H | trifluoroacetic acid |
| H | H | nitro | H | H | H | H | — |
| H | H | nitro | H | H | H | H | hydrogen chloride |
| H | H | nitro | H | H | H | H | trifluoroacetic acid |
| H | H | H | H | H | nitro | H | — |
| H | H | H | H | H | nitro | H | hydrogen chloride |
| H | H | H | H | H | nitro | H | trifluoroacetic acid |
| nitro | H | H | nitro | H | H | H | — |
| nitro | H | H | H | H | nitro | H | — |
| H | H | H | nitro | H | nitro | H | — |
| H | nitro | H | nitro | H | H | H | — |
| cyano | H | H | H | H | H | H | — |
| H | cyano | H | H | H | H | H | — |
| H | H | cyano | H | H | H | H | — |
| H | H | cyano | H | H | H | H | hydrogen chloride |
| H | H | H | cyano | H | H | H | — |
| H | H | H | cyano | H | H | H | trifluoroacetic acid |
| chloro | H | H | H | H | H | H | — |
| iodo | H | H | H | H | H | H | — |
| methoxy | H | H | H | H | H | H | — |
| bromo | H | H | H | H | H | H | — |
| H | H | H | iodo | H | H | H | — |
| H | cyano | H | nitro | H | H | H | — |
| cyano | H | H | nitro | H | H | H | — |
| chloro | H | H | nitro | H | H | H | — |
| H | H | bromo | nitro | H | H | H | — |
| chloro | methyl | H | nitro | H | H | H | — |
| H | chloro | H | acetamido | H | H | H | — |

The biologically active compositions of this invention may comprise, in addition to the compounds of the general formulae (I) and (II) described hereinabove, one or more other compounds having biological activity.

The compounds and compositions of the invention may be used for animal husbandry, agricultural or horticultural purposes and may be formulated in a variety of ways, depending upon the particular purpose for which they are to be used.

For most purposes liquid formulations to be used as sprays are most convenient and amongst these again aqueous liquid formulations are preferred. These sprays are generally aqueous solutions, dispersions, or emulsions, and may be prepared by dissolving the active ingredient or ingredients of general formulae (I) and (II) in a liquid inert carrier; suitable liquid inert carriers are solvents which are non-toxic to the media to which the formulation is to be applied. The compositions of our invention may comprise one or more wetting, dispersing, or emulsifying agents. Such compositions are normally diluted with water which may likewise contain one or more wetting, dispersing, or emulsifying agents. Suitable organic solvents are for example toluene, kerosene, methylated naphthalenes, xylenes, trichloroethylene, ethylene dichloride, isopropyl alcohol, diacetone alcohol and propylene glycol.

The compositions to be used as sprays may also be in the form of aerosols wherein the formulation is held in a container under pressure in the presence of a propellant such as dichlorodifluoromethane or fluorotrichloromethane.

Alternatively our compositions may also be formulated in the form of dusting powders or granules wherein the active ingredient is mixed with a solid inert carrier. Suitable solid inert carriers may be, for example, kaolin, powdered chalk, talcs, kieselguhr, dolomite, calcium carbonate, powdered magnesia, Fuller's earth, gypsum, Hewitt's earth, diatomaceous earth, china clay, bentonite, and other colloidal clays.

The compositions may also be in the form of dispersible powder or grains comprising, in addition to the active ingredient an inert carrier comprising a wetting agent to facilitate the dispersion of the powder or grains in liquids. Such powders or grains may include fillers, suspending agents and the like. The preferred dispersible powders comprise the active ingredient mixed with a finely ground colloidal clay together with a dispersing agent.

Suitable wetting agents, dispersing agents and emulsifying agents are known from the prior art and may be of the cationic, anionic or non-ionic type. Suitable agents of the cationic type include for example quaternary ammonium compounds such as cetyltrimethylammonium bromide. Suitable agents of the anionic type include for example soaps, salts of aliphatic monoesters of sulphuric acid, for example sodium lauryl sulphate, salts of sulphonated aromatic compounds, for example sodium dodecyl-benzene sulphonate, sodium, calcium, or ammonium lignosulphonate, butylnaphthalene sulphonate and a mixture of the sodium salts of di-isopropyl and tri-isopropylnaphthalene sulphonic acids. Suitable agents of the non-ionic type include for example the condensation products of an alkylene oxide such as ethylene oxide or propylene oxide with fatty alcohols such as oleyl alcohol or cetyl alcohol, or with alkylphenols such as octyl-phenol, nonyl-phenol and octyl-cresol. Other non-ionic agents are the partial esters derived from long chain fatty acids and hexitol anhydrides, the condensaion products of the said partial esters with an alkylene oxide such as ethylene oxide or propylene oxide and the lecithins.

Suitable suspending agents are for example, hydrophilic colloids, for example polyvinyl pyrrolidone and sodium carboxymethyl cellulose, and the vegetable gums, for example gum acacia and gum tragacanth.

By the inclusion of suitable additives, for example for improving the distribution, adhesive power, and resistance to rain on treated surfaces, the different compositions can be better adapted for the various uses for which they are intended.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods, and after such storage, to be capable of dilution with water so as to form aqueous preparations which remain homogeneous for a sufficient time to enable them to be applied by conventional spray equipment. Suitable formulations will depend on the nature of the active ingredient or ingredients and those most suited for any particular purpose may be determined by those persons skilled in the art by a few simple experiments. The concentrates may conveniently contain from 1 to 10% by weight of the active ingredient or ingredients and generally from 2 to 5% by weight of the active ingredient or ingredients. When diluted to form aqueous preparations, such preparations may contain varying amounts of the active ingredient or ingredients, depending upon the purpose for which they are to be used, but an aqueous preparation containing between 0.0001% and 1% by weight, preferably between 0.01 and 0.5% by weight may be used. A typical concentrate of this type would comprise 4% 5-nitro-isoquinoline and 96% of an alkyl aryl polyether alcohol dispersing agent, all quantities being expressed on a weight basis.

Preferred herbicidally active compositions are those comprising as active ingredient organic compounds of formula (I) wherein at least one of $R^1$, $R^3$, $R^4$, $R^5$, $R^6$, $R^7$ and $R^8$ is selected from the group consisting of halo, nitro, cyano, methyl, and acylamino groups.

More preferred herbicidally active compositions are those comprising as active ingredient isoquinolines of the formula (I) wherein $R^1$, $R^4$, $R^6$ and $R^8$ are each as above defined, $R^3$ is selected from the group consisting of hydrogen, halogen, and methyl, $R^5$ is selected from the group consisting of hydrogen, nitro, cyano, halogen, and acylamino, and $R^7$ is selected from the group consisting of hydrogen, cyano, and nitro, with the provisos that when $R^5$ is acylamino then of $R^1$, $R^3$, $R^4$, $R^6$ and $R^8$ at least one is halogen, and $R^5$ may be selected from the group consisting of hydrogen and halogen only when $R^7$ is selected from the group consisting of nitro and cyano.

Further preferred herbicidally active compositions are those comprising as active ingredient isoquinoline salts of the general formula (II) and wherein $R^1$, $R^4$, $R^6$, and $R^8$ are each as above defined, $R^3$ is selected from the group consisting of hydrogen, halogen, and methyl, $R^5$ is selected from the group consisting of hydrogen, nitro, cyano, halogen, and acylamino, $R^7$ is selected from the group consisting of hydrogen, cyano, and nitro, and HX is selected from the group consisting of hydrogen chloride, hydrogen bromide, hydrogen iodide, trifluoroacetic acid, monochlorodifluoroacetic acid, pentafluoropropionic acid, 2,6-dichloro-4-nitrophenol and trichloroacetic acid, with the provisos that when $R^5$ is acylamino then of $R^1$, $R^3$, $R^4$, $R^6$, and $R^8$ at least one is halogen, and $R^5$ may be selected from the group consisting of hydrogen and halogen only when $R^7$ is selected from the group consisting of nitro and cyano.

Further preferred herbicidally active compositions according to the present invention are those comprising as active ingredient isoquinolines of the general formula (I) wherein $R^1$, $R^4$, $R^6$, and $R^8$ are each hydrogen, $R^3$ is selected from the group consisting of hydrogen, methyl, and halogen, $R^5$ is selected from the group consisting of nitro, acylamino, and cyano, and $R^7$ is selected from the group consisting of hydrogen, nitro and cyano, with the proviso that when $R^5$ is acylamino, $R^3$ is halogen.

In addition, further preferred herbicidally active compositions according to the present invention are those comprising as active ingredient isoquinoline salts of the general formula (II), and wherein $R^1$, $R^4$, $R^6$ and $R^8$ are each hydrogen, $R^3$ is selected from the group consisting of nitro, acylamino, and cyano, $R^7$ is selected from the group consisting of hydrogen, nitro, and cyano, and HX is selected from the group consisting of hydrogen chloride, hydrogen bromide, hydrogen iodide, trifluoroacetic acid, monochlorodifluoroacetic acid, pentafluoropropionic acid, 2,6-dichloro-4-nitrophenol, and trichloroacetic acid, with the proviso that when $R^5$ is acylamino, $R^3$ is halogen.

Most preferred herbicidally active compositions according to the present invention are those comprising as active ingredient a compound selected from the group consisting of 3-chloro-5-acetamido-isoquinoline and the hydrochloride, hydrobromide, hydro-iodide, trifluoroacetate, monochlorodifluoroacetate, pentafluoropropionate, 2,6-dichloro-4-nitro-phenoxide and trichloroacetate salts thereof.

Especially preferred herbicidally active compositions according to the present invention are those comprising as active ingredient 3-chloro-5-acetamidoisoquinoline.

As stated above the compounds and compositions of this invention have useful herbicidal properties; thus compounds of the formulae:

applications, as selective weed killers, and for either pre- or post- emergent weed control. The compounds control both annual and perennial broad-leaved weeds and grasses, and they may be applied to weeds growing in economic crops, to obtain selective results. In particular the isoquinoline compounds of formulae (I) and (II) are effective in regulating the growth of wild oats, wheat, barley, wimmera rye grass, phalaris, lucerne, wild mustard, peas, safflower, cotton, oil seed rape, linseed, lupin, soya bean and carrots.

The amount of isoquinoline compound used as herbicide will depend on the vegetation conditions, the degree of control desired, the formulation used, the nature of the compound, the mode of application, the climate and the season of the year at the time of application, the rainfall during the treatment period and other variables. We have found that in general, quantities of active ingredient ranging from 0.25 to 10 lb/acre are required for pre-emergence control; usually 1 pound per acre is effective, while 1 – 2 pounds per acre is a preferred quantity. For soil foliage applications we have found that larger amounts are generally necessary; 4 pounds per acre generally being required, while the preferred amount applied for this purpose is generally 5 – 10 pounds per acre.

Accordingly we provide a process of controlling or eradicating undesired vegetation, which process comprises treating areas infested with undesired vegetation, with the compounds and compositions according to this invention.

Preferred insecticidal and acaricidal compositions are those comprising as active ingredient organic compounds of general formula (I) hereinabove, wherein at least one of $R^1$, $R^3$, $R^4$, $R^5$, $R^6$, $R^7$ and $R^8$ are selected from the group consisting of fluoro, chloro, bromo, methyl, n-butyl, nitro, amino and cyano groups.

Most preferred insecticidal and acaricidal compositions are those comprising as active ingredient compounds of formula (I) hereinabove, wherein $R^1$, $R^3$, $R^4$, $R^6$, $R^7$ and $R^8$ are each hydrogen, and $R^5$ is selected from the group consisting of chloro, nitro, cyano and amino groups.

Further preferred insecticidal and acaricidal compositions according to the present invention are those comprising as active ingredient isoquinoline salts of general formula (II) hereinabove, and wherein $R^4$, $R^6$, $R^7$ and $R^8$ are each hydrogen, $R^1$ is selected from the group consisting of hydrogen, methyl, and n-butyl, $R^3$ is selected from the group consisting of hydrogen, chloro and amino, $R^5$ is selected from the group consisting of hydrogen, nitro, fluoro, chloro, bromo, cyano and methyl, and HX is selected from the group consisting of hydrogen chloride, hydrogen, bromide, hydrogen iodide, trifluoroacetic acid, monochlorodifluoroacetic acid, pentafluoropropionic acid, pentachlorophenol,

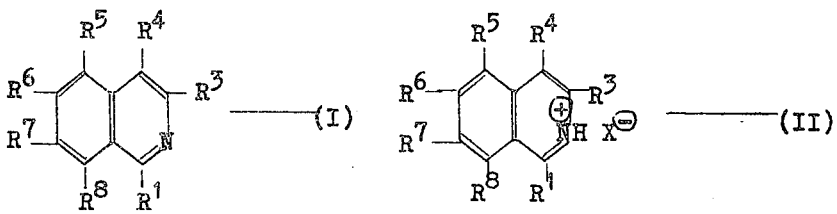

wherein $R^1$, $R^3$, $R^4$, $R^5$, $R^6$, $R^7$, and $R^8$ and HX are as defined hereinabove, have shown high activity as general purpose weed killers, soil sterilants, in soil foliage 2,4-dinitro-phenol, 2,6-dichloro-4-nitro-phenol, 2,6-dibromo-4-nitro-phenol, and tetrabromo-m-cresol.

As stated hereinabove the compounds and compositions of this invention have useful insecticidal and acaricidal properties; thus the compounds of general formulae (I) and (II) hereinabove have shown high contact and residual activity against various species of insects, mites, and ticks, e.g. *Musca domestica* (house fly), *Lucilia cuprina* (sheep blow fly), *Plutella maculipennis* (cabbage moth), *Cydia pomonella* (codling moth), *Tortrix postvittana* (light brown apple moth), *Tetranychus telarius* (red spider), *Calandra granaria* (grain weevil), *Pseudoccus maritimus* (mealy bug), *Aphis craccivora* (cowpea aphid), *Thorimaea operculella* (potato moth), *Aonidiella aurontii* (red scale), *Tribolium confusium* (confused flower beetle) and *Boophilus microplus* (cattle tick).

The amount of isoquinoline compound used as insecticide or acaricide depends amongst other things on the compound selected, the species and strain of insects or acarina to be controlled, the type of formulation to be applied and the conditions under which it is applied. We have found that generally, insecticidally and acaricidally effective compositions according to our invention comprise from 0.0001% w/w to 2.0% w/w of active ingredient based on weight of the total composition and preferably comprise between 0.05% w/w and 1.0% w/w based on the weight of the total composition.

Accordingly we provide a process of controlling or eradicating undesired insects, which process comprises treating media infested with insects with the compounds and compositions according to this invention.

We also provide a process of controlling or eradicating undesired acarina, which process comprises treating media including plants and animals infested with acarina with the compounds and compositions according to this invention.

Preferred fungicidally active compositions according to our invention are those comprising as active ingredient organic compounds of formula (I) hereinabove, wherein at least one of $R^1$, $R^3$, $R^4$, $R^5$, $R^6$, $R^7$ and $R^8$ is selected from the group consisting of fluoro, chloro, bromo, iodo, cyano, nitro, amino, methyl and n-butyl groups.

More preferred fungicidal compositions according to the present invention are those comprising as active ingredient organic compounds of formula (I) hereinabove, and wherein $R^1$ is selected from the group consisting of hydrogen and methyl, $R^3$ is selected from the group consisting of hydrogen, chloro, amino, and methyl, $R^4$ is selected from the group consisting of hydrogen, chlorine, bromine, and iodine, $R^5$ is selected from the group consisting of chloro, amino, and nitro, $R^6$ and $R^7$ are each hydrogen, and $R^8$ is selected from the group consisting of hydrogen and nitro.

Further preferred fungicidally active compositions according to the present invention are those comprising as active ingredient isoquinoline salts of general formula (II) and wherein $R^1$ is selected from the group consisting of hydrogen and methyl, $R^3$ is selected from the group consisting of hydrogen and methyl, $R^4$ is selected from the group consisting of hydrogen, chloro, bromo, and iodo, $R^5$ is selected from the group consisting of hydrogen, nitro, amino, and chloro, $R^6$, $R^7$ and $R^8$ are each hydrogen, and HX is selected from the group consisting of hydrogen chloride, hydrogen bromide, hydrogen iodide, trifluoroacetic acid, pentachlorophenol, 2,6-dibromo-4-nitro-phenol and tetrabromo-m-cresol.

Most preferred fungicidal compositions according to the present invention are those comprising as active ingredient a compound selected from the group consisting of 4-bromo-5-nitro-isoquinoline and the hydrogen chloride, hydrogen bromide, hydrogen iodide, trifluoroacetic acid, pentachlorophenoxide, 2,6-dibromo-4-nitro-phenoxide, and tetrabromo-m-cresoxide salts thereof.

Especially preferred fungicidal compositions according to the present invention are those comprising as active ingredient 4-bromo-5-nitro-isoquinoline.

As stated hereinabove the compounds and compositions of this invention have useful fungicidal properties; thus we have found that the compounds of general formulae (I) and (II) hereinabove are effective in eradicating or controlling undesired fungi, for example *Venturia inaquelis* (black spot), *Ustilago hordei* (covered smut), *Tilletia foetida* (stinking bunt of wheat), *Peronospora tabacina* (blue mould of tobacco), *Erysiphe graminis* (wheat powdery mildew), *Alternaria solani* (early blight of tomatoes) and *Puccinia coronata* (oat rust).

The amount of isoquinoline compound required for effective control of fungi depends amongst other things on the active ingredients selected, the strains of fungi to be treated, the degree of control required, the type of medium infected, the type of formulation used, and the conditions under which it is applied. We have found that generally, 1 ppm of the isoquinoline compounds according to our invention based on the weight of the total composition is effective for control of fungi, while our preferred concentration range is from 5 ppm to 1000 ppm, based on the weight of the total composition.

Accordingly we provide a process of controlling or eradicating undesired fungi, which proces comprises treating media infested with fungi with compositions according to our invention.

Certain of the compounds of general formula (I) described hereinabove are novel and are useful as intermediates in the preparation of isoquinoline salts or exhibit biological activity.

Accordingly we provide new compounds of the general formula:

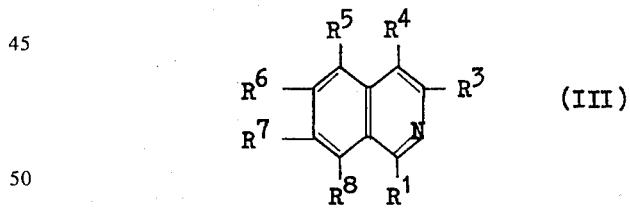

wherein, of $R^1$, $R^3$, $R^4$, $R^5$, $R^6$, $R^7$ and $R^8$, when any two are nitro, or cyano, or any one is cyano and any other one nitro, then the remainder are hydrogen; and wherein when any one of $R^1$, $R^3$, $R^4$, $R^5$, $R^6$, $R^7$ and $R^8$ is halogen, and any other one alkyl and any other one nitro, then the remainder are hydrogen with the proviso that when $R^1$ is methyl, and $R^5$ is chloro, $R^8$ may not be nitro; and wherein when $R^3$ is chloro and $R^1$, $R^4$, $R^6$, $R^7$ and $R^8$ are each hydrogen, then $R^5$ is selected from the group consisting of fluoro, chloro, nitro, and amino and acylamino; and wherein when $R^5$ is nitro, and $R^3$, $R^4$, $R^6$, $R^7$ and $R^8$ are each hydrogen, then $R^1$ is n-butyl; and wherein when $R^3$ is nitro, then $R^1$, $R^4$, $R^5$, $R^6$, $R^7$ and $R^8$ are each hydrogen; and wherein when $R^3$ is methyl and $R^8$ is nitro, then $R^1$, $R^4$, $R^5$, $R^6$ and $R^7$ are each hydrogen.

Further we provide as new compounds isoquinoline salts of the general formula:

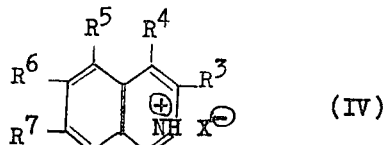

wherein each of $R^1$, $R^3$, $R^4$, $R^5$, $R^6$, $R^7$ and $R^8$ are selected from the group consisting of hydrogen, alkyl, halo, nitro, amino, mono- and di-alkyl substituted amino, mono- and di-aryl substituted amino, acyl substituted amino, cyano, arylthio, alkylthio, alkoxy, and amine salt groups of the formula:

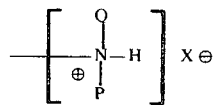

wherein P and Q are as defined hereinabove for the isoquinoline salts of general formula (II) and HX is as defined hereinbelow, with the proviso that if $R^3$ is amino or substituted amino, then $R^1$ may not be halogen, alkylthio or arylthio; and HX may be any inorganic acid, organic acid, or acidic phenol capable of forming a salt with the isoquinoline nucleus, with the provisos that HX may not be hydrogen chloride or sulphuric acid except when at least one of $R^1$, $R^3$, $R^4$, $R^5$, $R^6$, $R^7$ and $R^8$ is a nitro, acylamino, or cyano group, that if each of $R^1$, $R^3$, $R^4$, $R^5$, $R^6$, $R^7$ and $R^8$ is hydrogen then HX may not be an inorganic acid, and that HX may not be chloroplatinic acid, perchloric acid, picric acid, picrolinic acid, maleic acid, p-toluene-sulphonic acid, or thiocyanic acid.

The compounds of our invention as disclosed hereinabove can be prepared by methods known in the art for analogous compounds.

Thus, for example, for the preparation of the compounds of formula (I) and (III) described hereinabove, nitro groups may be introduced into the isoquinoline nucleus by the known method of reaction with a mixture of concentrated sulphuric acid and potassium nitrate followed by working up in the normal manner; amino-isoquinolines may be obtained in known manner by reduction of the corresponding nitro derivative; halo and poly-halo isoquinolines may be prepared in known manner by diazotisation of the corresponding aminoisoquinoline, followed by reaction with an appropriate cuprous halide according to the Sandmeyer reaction; or by a Schiemann reaction, or from homophthalimide by the method of Osborn and Schofield (J.C.S. (1956) p. 4191); and alkyl groups may be introduced by treatment of the isoquinoline nucleus with the appropriate alkyl lithium compound followed by hydrolysis and dehydrogenation.

The isoquinoline salts of formulae (II) and (IV) may be prepared by dissolving the free base, prepared as described hereinabove, in an excess of the appropriate acid, where the acid is in liquid form, then evaporating the mixture to dryness, slurrying the residue with a lower alcohol for example, ethanol, filtering and recrystallizing the filter cake from a suitable solvent.

Alternatively the free base, prepared as described hereinabove, may be mixed with the appropriate acid in the presence of a solvent chosen to precipitate the salt. The salt is then filtered off, and recrystallized from a suitable solvent.

The following examples illustrate the preparation of the compounds and compositions of our invention, and their biological effects, but are not to be construed as limiting.

EXAMPLE 1

This example illustrates the preparation of 3-chloro-5-nitro-isoquinoline having the formula:

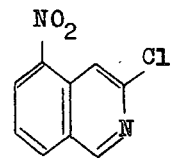

3-chloro-isoquinoline (16.35 g., 0.1 mole) was dissolved in concentrated sulphuric acid (80 ml) and the solution was cooled to approximately 5°C in an ice-water bath. Potassium nitrate (11 g. 0.11 mole) was dissolved in concentrated sulphuric acid (60 ml), the solution was cooled to approximately 5°C and added dropwise, with stirring, over a period of 2 hours to the 3-chloro-isoquinoline solution, the temperature of the reaction mixture being maintained in the region of from 3 to 8°C by means of the ice-water bath. The bath was then removed and the mixture stirred for a further 2 hours, and allowed to stand overnight. Next day the reaction mixture was poured into a water (800 ml)-ice (800 g.) mixture, and 3-chloro-5-nitro-isoquinoline precipitated as fine white crystals. The precipitate was filtered off, slurried with water, filtered again, washed thoroughly with water, and then recrystallized from a 3:1 v/v mixture of ethanol/acetone to yield 16.33 g. of 3-chloro-5-nitro-isoquinoline of melting point 163° – 164°C.

EXAMPLE 2

1-n-butyl-5-nitro-isoquinoline having the formula:

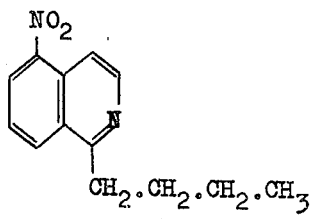

was prepared by the procedure of Example 1, except that the 3-chloro-isoquinoline of that example was replaced by 0.1 mole of 1-n-butyl-isoquinoline to yield 1-n-butyl-5-nitro-isoquinoline of melting point 69° – 69.5°C.

EXAMPLE 3

1,5-dinitro-isoquinoline having the formula:

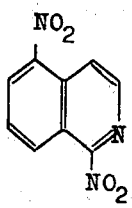

was prepared by the procedure of Example 1, except that the 3-chloro-isoquinoline of that example was replaced by 0.1 mole of 1-nitro-isoquinoline to yield 1,5-dinitro-isoquinoline melting over the range 195° – 200°C. The product was not recrystallized.

EXAMPLE 4

This example illustrates the preparation of 4-bromo-5-nitro-isoquinoline having the formula:

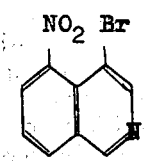

4-bromo-isoquinoline (10.4 g) was dissolved in concentrated sulphuric acid (50 ml) and the solution was cooled to approximately 5°C. A solution of potassium nitrate (8.6 g) in concentrated sulphuric acid (50 ml) was then added in dropwise fashion to maintain the temperature of the reaction mixture in the range 0°C to 10°C. After the addition was completed the reaction mixture was poured onto a mixture of ice (300 g) and water (300 ml), and ammonia was then slowly added until the mixture became alkaline. The reaction mixture was then filtered, and the yellow material thus isolated was washed with water and allowed to dry, to provide 9.0 g of 4-bromo-5-isoquinoline, melting at 177° – 178°C.

EXAMPLE 5

This example illustrates the preparation of 3-methyl-8-nitro-isoquinoline having the formula:

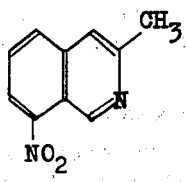

This compound is produced in small quantities along with its isomer 3-methyl-5-nitro-isoquinoline when a sulphuric acid solution of 3-methyl-isoquinoline is treated with potassium nitrate dissolved in sulphuric acid according to the method of Example 1. This example illustrates the separation and isolation of 3-methyl-8-nitro-isoquinoline and 3-methyl-5-nitro-isoquinoline.

Thus a mixture of compounds of the formulae:

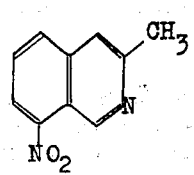 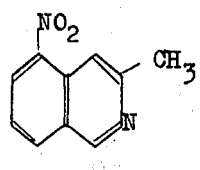

(V)  (VI)

was prepared by the procedure of Example 1, except that the 3-chloro-isoquinoline of that example was replaced by 0.1 mole of 3-methyl-isoquinoline and no purification was attempted.

The crude reaction product was recrystallized from ethanol to yield a yellow solid A and a filtrate B. The filtrate B was discarded. The solid A was found to melt in two portions: 87° – 90°C and 96° – 106°C. Thin layer chromatography tests indicated that two compounds were in fact present.

The solid A was again recrystallized from ethanol to yield a solid $A^1$ and a filtrate $B^1$. The volume of $B^1$ was reduced to half, chilled in an ice bath and filtered to yield a solid $A^2$ and filtrate $B^2$. This process was repeated with the filtrate $B^2$ to yield a solid $A^3$ and filtrate $B^3$.

The solid $A^1$ was again recrystallized from ethanol to yield crystals of melting point 107° – 108.5°C. The melting point and infra-red and nuclear magnetic resonance data indicated that this compound was 3-methyl-5-nitro-isoquinoline. The solid $A^2$ was discarded.

The solid $A^3$ was dissolved in a small quantity of ethyl acetate and column chromatographed over silica gel with ethyl acetate. Fourteen ethyl acetate fractions were collected from the column, and thin layer chromatography tests were run on each of these fractions. The tests indicated the presence of one compound in fractions numbered 5 to 11 inclusive, and another compound in fractions numbered 13 and 14.

Fractions numbered 13 and 14 were combined and evaporated to yield a yellow solid of m.p. 108°C., analysis of which by infra-red spectroscopy and nuclear magnetic resonance showed that the compound was 3-methyl-5-nitro-isoquinoline.

The fractions numbered 5 to 11 inclusive were combined and the solvent was removed under reduced pressure to yield a yellow crystalline solid of melting point 142.5°C to 143.5°C. By infra-red spectroscopy and nuclear magnetic resonace it was shown that this compound was 3-methyl-8-nitro-isoquinoline.

EXAMPLE 6

This example illustrates the preparation of 5,8-dinitro-isoquinoline having the formula:

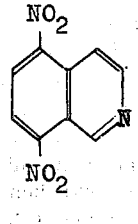

5-nitro-isoquinoline (5 g) was dissolved in concentrated sulphuric acid (50 ml) and potassium nitrate (10 g) was added. The mixture was then heated at 180°C for seven hours, allowed to cool to room temperature (20°C), and then poured onto 100 ml of an ice/water mixture.

This aqueous reaction mixture was made alkaline with ammonia, and then extracted with methylene dichloride. The methylene dichloride extract was dried, the solvent was evaporated off, and the residue thus obtained was recrystallized from benzene, to yield 0.6 g of product melting at 241° – 242°C.

Nuclear magnetic resonance spectra confirmed that the product was 5,8-dinitro-isoquinoline.

EXAMPLE 7

This example illustrates the preparation of 3-chloro-5-amino-isoquinoline having the formula:

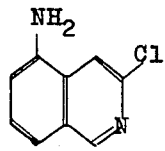

3-chloro-5-nitro-isoquinoline (20.9 g., 0.1170 mole, prepared according to the method of Example 1 hereinabove) was suspended in glacial acetic acid (160 ml), and water (160 ml) was then added while the temperature of the mixture was being raised to 60°C. Keeping the temperature between 60° and 70°C, powdered iron (15.2 g) was added slowly to the stirred mixture, and stirring was continued for 2 hours after addition of the iron was completed. The reaction mixture was allowed to stand overnight, and was then made alkaline with 20% w/v aqueous sodium hydroxide solution, and filtered. The residue was dried overnight, over silica gel in a vacuum oven at 50°C. The dried cake was then broken up and extracted — three times with ether under reflux. The ether extract was boiled with charcoal, dried over anhydrous sodium sulphate, filtered, and the ether evaporated off to yield 9.25 g of 3-chloro-5-amino-isoquinoline of m.p. 176° – 177°C. Further ether extraction of the filter cake yielded another 4.2 g of 3-chloro-5-amino-isoquinoline of m.p. 175°–177°C.

EXAMPLE 8

This example illustrates the preparation of 3-chloro-5-acetamido-isoquinoline having the formula:

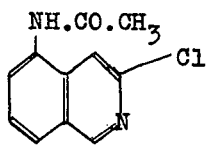

3-chloro-5-amino-isoquinoline (6 g) was dissolved in glacial acetic acid (20 ml), and acetic anhydride (4 g) was added dropwise. The temperature of the reaction mixture rose to 30°C and it solidified. The reaction mixture was placed on a filter, washed with a small quantity of glacial acetic acid and then with a small quantity of diethyl ether, and then allowed to dry, to yield 6.7 g of product melting at 207.5° – 208°C.

Infra-red and nuclear magnetic resonance spectra confirmed that the product was 3-chloro-5-acetamido-isoquinoline.

EXAMPLE 9

This example illustrates the preparation of 3-chloro-5-fluoro-isoquinoline having the formula:

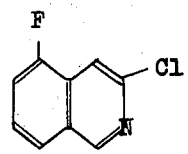

3-chloro-5-amino-isoquinoline (12 g) was dissolved in a mixture of 40% fluoroboric acid (150 ml) and ethanol (130 ml), and then 5.3 g of a cold saturated aqueous solution of sodium nitrite was added. Diethyl ether (65 ml) was then added to precipitate the diazonium fluoroborate salt of the 3-chloro-5-amino-isoquinoline.

The diazonium fluoroborate salt was washed with an ethanol/diethyl ether mixture and allowed to dry, and the solid product was heated until the evolution of nitrogen ceased. The residue was added to a small quantity of water, and sufficient aqueous 20% w/v sodium hydroxide was added to render the mixture strongly alkaline. This reaction mixture was then steam distilled, and the distillate was extracted with dietyhyl ether. The ether extract was dried, and the solvent was then evaporated off to yield 6.7 g of 3-chloro-5-fluoro-isoquinoline, melting over the range 64° – 66°C.

EXAMPLE 10

This example illustrates the preparation of 1-chloro-3-methyl-5-nitro-isoquinoline having the formula:

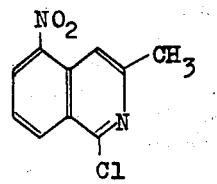

3-methyl-5-nitro-isoquinoline-2-oxide (12 g) was added to phosphorus oxychloride (60 ml) and the mixture was refluxed with stirring for 1 hour, and then allowed to cool to room temperature (20°C). The reaction mixture was then poured onto ice, and the crude product, weighing 6.2 g, was isolated by filtration. This product was then recrystallized twice from acetone to yield 1-chloro-3-methyl-5-nitro-isoquinoline melting at 112°C.

EXAMPLE 11

This example illustrates the preparation of 3-methyl-5-nitro-isoquinoline hydrochloride, having the formula:

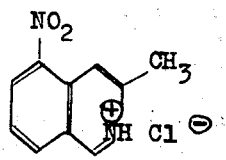

3-methyl-5-nitro-isoquinoline (6 g), prepared according to the method of Example 5 hereinabove, was dissolved in concentrated hydrochloric acid (30 ml). The excess acid was then removed by means of a rotary evaporator, and the residue was digested with boiling ethanol (100 ml). The mixture was cooled and filtered, and the residue was dried in vacuo for several hours, to yield 6.9 g of 3-methyl-5-nitro-isoquinoline hydrochloride melting over a temperature range from 178° to 183°C.

EXAMPLES 12 TO 18 INCLUSIVE

Compounds of the formula:

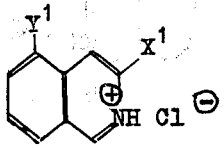

were prepared by the procedure of Example 11 except that the 3-methyl-5-nitro-isoquinoline of that example was replaced by the appropriate substituted isoquinoline to yield compounds of the above formula, and wherein the substituents $X^1$ and $Y^1$ are listed in Table II below.

TABLE II

| Example Number | $X^1$ | $Y^1$ | Melting point of Product (°C) |
|---|---|---|---|
| 12 | —Cl | —H | 106 – 116 |
| 13 | —H | —H | 164 – 172 |
| 14 | —CH₃ | —H | 178 – 180 |
| 15 | —H | —NO₂ | 169 – 175 |
| 16 | —H | —Br | 167 – 171 |
| 17 | —H | —F | 170 – 180 |
| 18 | —H | —Cl | 167 – 182 |

EXAMPLE 19

1-Chloro-isoquinoline hydrochloride having the formula:

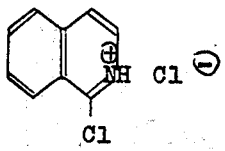

was prepared by the procedure of Example 11 except that the 3-methyl-5-nitro-isoquinoline of that example was replaced by 1-chloro-isoquinoline to yield 1-chloro-isoquinoline hydrochloride melting over the range 78° – 84°C.

EXAMPLE 20

4-Cyano-isoquinoline hydrochloride having the formula:

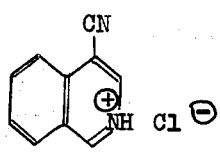

was prepared by the procedure of Example 11 except that the 3-methyl-5-nitro-isoquinoline of that example was replaced by 4-cyano-isoquinoline to yield 4-cyano-isoquinoline hydrochloride, melting at 105°C.

EXAMPLES 21 TO 23 INCLUSIVE

Compounds of the formula:

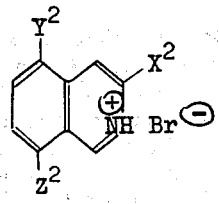

were prepared by the procedure of Example 11 hereinabove, except that the 3-methyl-5-nitro-isoquinoline of that example was replaced by the appropriate substituted isoquinoline, and the concentrated hydrochloric acid of Example 11 was replaced by concentrated hydrobromic acid, to yield compounds of the above formula, and wherein the substituents $X^2$, $Y^2$ and $Z^2$ are listed in Table III below.

TABLE III

| Example Number | $X^2$ | $Y^2$ | $Z^2$ | Melting point of Product (°C) |
|---|---|---|---|---|
| 21 | —CH₃ | —NO₂ | H | 149 – 151 |
| 22 | —H | —Cl | —NO₂ | 199 – 203 |
| 23 | —CH₃ | —H | —NO₂ | 198 – 207 |

EXAMPLES 24 TO 27 INCLUSIVE

Compounds of the formula:

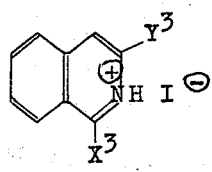

were prepared by the procedure of Example 11 hereinabove, except that the 3-methyl-5-nitro-isoquinoline of that example was replaced by the appropriate substituted isoquinoline, and the concentrated hydrochloric acid of Example 11 was replaced by concentrated hydriodic acid, to yield compounds of the above formula, and wherein the substituents $X^3$ and $Y^3$ are listed in Table IV below.

TABLE IV

| Example Number | $X^3$ | $Y^3$ | Melting point of Product (°C) |
|---|---|---|---|
| 24 | —H | —H | 170 – 175 |
| 25 | —H | —CH₃ | 174 |
| 26 | —CH₃ | —H | 166 – 178 |
| 27 | —Cl | —H | 86 – 88 |

EXAMPLE 28

5-Chloro-8-nitro-isoquinoline hydro-iodide having the formula:

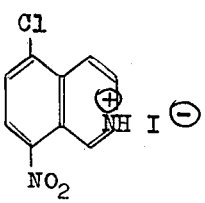

was prepared by the procedure of Example 11 hereinabove, except that the 3-methyl-5-nitro-isoquinoline of that example was replaced by 5-chloro-8-nitro-isoquinoline, and the concentrated hydrochloric acid of Example 11 was replaced by concentrated hydriodic acid, to yield 5-chloro-8-nitro-isoquinoline hydroiodide, melting over the range 161°–5°C.

EXAMPLE 29

This example illustrates the preparation of 5-nitro-isoquinoline hydrobromide having the formula:

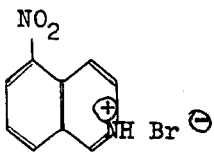

5-nitro-isoquinoline (3 g) was dissolved in warm ethanol (40 ml) and hydrogen bromide was added (4.5 ml of a 48% w/v aqueous solution). The salt precipitated immediately, and the reaction mixture was cooled to room temperature, filtered, the residue washed with ethanol, and dried, to yield 3.95 g of 5-nitro-isoquinoline hydrobromide of melting point 250.5°C.

EXAMPLE 30

3-Chloro-isoquinoline hydrobromide, having the formula:

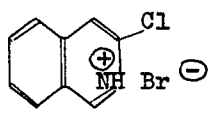

was prepared by the procedure of Example 29 hereinabove, except that the 5-nitro-isoquinoline of that example was replaced with 3-chloro-isoquinoline to yield 3-chloro-isoquinoline hydrobromide, melting over the range 146° – 156°C.

EXAMPLE 31

1-Methyl-5-nitro-isoquinoline hydrobromide, having the formula:

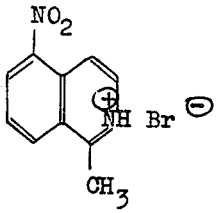

was prepared by the procedure of Example 29 hereinabove,, except that the 5-nitro-isoquinoline of that example was replaced with 1-methyl-5-nitro-isoquinoline to yield 1-methyl-5-nitro-isoquinoline hydrobromide, melting at 239°C.

EXAMPLES 32 TO 36 INCLUSIVE

Compounds of the formula:

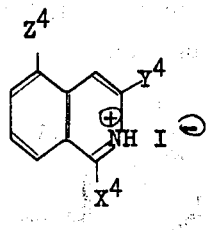

were prepared by the procedure of Example 29 hereinabove, except that the 5-nitro-isoquinoline was replaced by the appropriate substituted isoquinoline, and the hydrogen bromide was replaced by hydrogen iodide, to yield compounds of the above formula, and wherein the substituents $X^4$, $Y^4$ and $Z^4$ are listed in Table V below.

TABLE V

| Example Number | $X^4$ | $Y^4$ | $Z^4$ | Melting range of Product (°C) |
|---|---|---|---|---|
| 32 | —H | —CH$_3$ | —NO$_2$ | 180 – 188 |
| 33 | —H | —H | —NO$_2$ | 174 – 178 |
| 34 | —CH$_3$ | —H | —NO$_2$ | 173 – 178 |
| 35 | —n—C$_4$H$_9$ | —H | —NO$_2$ | 140 – 148 |
| 36 | —H | —Cl | —H | 142 – 153 |

EXAMPLES 37 TO 47 INCLUSIVE

Compounds of the formula:

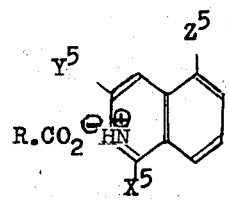

were prepared by the procedure of Example 29 hereinabove, except that the 5-nitro-isoquinoline of that example was replaced by the appropriate substituted isoquinoline, and the hydrogen bromide was replaced with an ehtanolic solution of the appropriate carboxylic acid, to yield compounds of the above formula, and wherein substituents $X^5$, $Y^5$, $X^5$ and R, are listed below in Table VI.

TABLE VI

| Example Number | $X^5$ | $Y^5$ | $Z^5$ | R | Melting point of Product (°C) |
|---|---|---|---|---|---|
| 37 | —H | —H | —H | CF$_3$— | 118 |
| 38 | —H | —H | —NO$_2$ | CF$_3$— | 109–111 |
| 39 | —H | —CH$_3$ | —NO$_2$ | CF$_3$— | 111–112 |

TABLE VI-continued

| Example Number | X⁵ | Y⁵ | Z⁵ | R | Melting point of Product (°C) |
|---|---|---|---|---|---|
| 40 | —CH₃ | —H | —NO₂ | CF₃— | 124–128 |
| 41 | —H | —H | —H | CCl₃— | 89–90.5 |
| 42 | —H | —H | —H | CClF₂— | 95–100 |
| 43 | —H | —H | —NO₂ | CClF₂— | 93.5 |
| 44 | —H | —H | —H | CH₃.CCl₂— | 55–57 |
| 45 | —H | —H | —NO₂ | CF₃.CF₂— | 98–100 |
| 46 | —H | —H | —NO₂ | 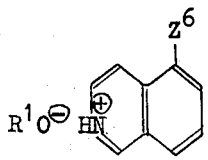 | 183–187 |
| 47 | —H | —H | —CN | CF₃— | >140 |

EXAMPLES 48 TO 53 INCLUSIVE

Compounds of the formula:

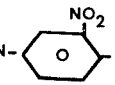

were prepared by the procedure of Example 29 hereinabove, except that the 5-nitro-isoquinoline of that example was replaced by the appropriate isoquinoline compound, and the hydrogen bromide was replaced with an ethanolic solution of the appropriate substituted phenol, to yield compounds of the above formula, and wherein the substituents $Z^6$ and $R^1$ are listed below in Table VII.

TABLE VII

| Example Number | Z⁶ | R¹ | Melting range of Product (°C) |
|---|---|---|---|
| 48 | —H | 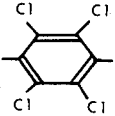 | 114–119 |
| 49 | —NO₂ | 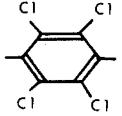 | 158–167 |
| 50 | —NO₂ | 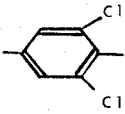 | 131–133 |
| 51 | —NO₂ | 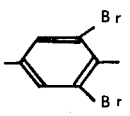 | 146–147 |
| 52 | —NO₂ | 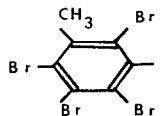 | 139–140 |
| 53 | —NO₂ | 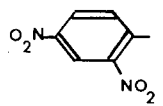 | 103–105 |

EXAMPLE 54

1-Methyl-isoquinolinium pentachlorophenoxide having the formula:

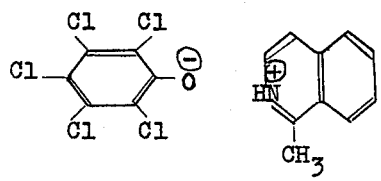

was prepared by the procedure of Example 29 hereinabove, except that the 5-nitro-isoquinoline of that example was replaced by 1-methyl-isoquinoline and the hydrogen bromide was replaced by an ethanolic solution of pentachlorophenol, to yield 1-methyl-isoquinolinium pentachlorophenoxide melting over the range 148° – 150°C.

EXAMPLE 55

5-Amino-isoquinoline dihydro-iodide having the formula:

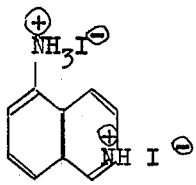

was prepared by the procedure of Example 29 hereinabove, except that the 5-nitro-isoquinoline of that example was replaced by 5-amino-isoquinoline, and the hydrogen bromide was replaced with hydrogen iodide to yield 5-aminoisoquinoline dihydro-iodide melting over the temperature range 184°C to 193°C.

EXAMPLE 56

Formulations of the compounds of the invention were prepared to give a 4% w/v concentration of active ingredient, and these were diluted with water to give concentrations of the active ingredient suitable for demonstrating biological activity. The concentrated formulations were prepared as follows.

Four parts by weight of the compound of the invention were added to 96 parts by weight of "Lubrol" E (a registered trade mark for a condensation product of alkylphenol with ethylene oxide) and the mixture was ball milled to produce a stable suspension. The concentrated suspension was then diluted with water to give aqueous sprayable compositions containing 0.05, 0.1 and 0.2% w/v of active material.

The compounds used in this example and the following examples 57 to 71 inclusive are designated numerically in Table VIII below.

TABLE VIII

| No. | Compound |
|---|---|
| 1 | isoquinoline |
| 2 | isoquinoline hydrochloride |
| 3 | isoquinoline hydrobromide |
| 4 | isoquinoline hydro-iodide |
| 5 | isoquinolinium trichloroacetate |
| 6 | isoquinolinium trifluoroacetate |
| 7 | isoquinolinium α, α-dichloropropionate |
| 8 | isoquinolinium hydrogen sulphate |
| 9 | isoquinolinium pentachlorophenoxide |
| 10 | 1-chloro-isoquinoline |
| 11 | 1-chloro-isoquinoline hydrochloride |
| 12 | 1-chloro-isoquinoline hydro-iodide |
| 13 | 1,3-dichloro-isoquinoline |
| 14 | 1,3-dichloro-5-nitro-isoquinoline |
| 15 | 1,3-dichloro-5-amino-isoquinoline |
| 16 | 1-chloro-5-nitro-isoquinoline |
| 17 | 1-chloro-3-methyl-5-nitro-isoquinoline |
| 18 | 1,3-dibromo-isoquinoline |
| 19 | 1-iodo-isoquinoline |
| 20 | 1-iodo-isoquinoline hydro-iodide |
| 21 | 1-methyl-isoquinoline |
| 22 | 1-methyl-isoquinoline hydro-iodide |
| 23 | 1-methyl-5-nitro-isoquinoline |
| 24 | 1-methyl-5-nitro-isoquinoline hydrobromide |
| 25 | 1-methyl-5-nitro-isoquinoline hydro-iodide |
| 26 | 1-methyl-5-nitro-isoquinolinium trifluoroacetate |
| 27 | 1-methyl-isoquinolinium pentachlorophenoxide |
| 28 | 1-n-butyl-isoquinoline |
| 29 | 1-n-butyl-5-nitro-isoquinoline |
| 30 | 1-n-butyl-5-nitro-isoquinoline hydro-iodide |
| 31 | 1-cyano-isoquinoline |
| 32 | 1-nitro-isoquinoline |
| 33 | 1,5-dinitro-isoquinoline |
| 34 | 3-chloro-isoquinoline |
| 35 | 3-chloro-isoquinoline hydrochloride |
| 36 | 3-chloro-isoquinoline hydrobromide |
| 37 | 3-chloro-isoquinoline hydro-iodide |
| 38 | 3-chloro-5-acetamido-isoquinoline |
| 39 | 3-chloro-5-fluoro-isoquinoline |
| 40 | 3-chloro-5-nitro-isoquinoline |
| 41 | 3-bromo-isoquinoline |
| 42 | 3-methyl-isoquinoline |
| 43 | 3-methyl-isoquinoline hydro-iodide |
| 44 | 3-methyl-5-nitro-isoquinoline |
| 45 | 3-methyl-5-nitro-isoquinoline hydrochloride |
| 46 | 3-methyl-5-nitro-isoquinoline hydrobromide |
| 47 | 3-methyl-5-nitro-isoquinoline hydro-iodide |
| 48 | 3-methyl-5-nitro-isoquinolinium trifluoroacetate |
| 49 | 3-methyl-8-nitro-isoquinoline hydrobromide |
| 50 | 3-amino-isoquinoline |
| 51 | 4-bromo-isoquinoline |
| 52 | 4-bromo-5-nitro-isoquinoline |
| 53 | 5,8-dinitro-isoquinoline |
| 54 | 4-cyano-isoquinoline |
| 55 | 4-cyano-isoquinoline hydrochloride |
| 56 | 5-fluoro-isoquinoline |
| 57 | 5-fluoro-isoquinoline hydrochloride |
| 58 | 5-chloro-isoquinoline |
| 59 | 5-chloro-isoquinoline hydrochloride |
| 60 | 5-chloro-8-nitro-isoquinoline |
| 61 | 5-chloro-8-nitro-isoquinoline hydrobromide |
| 62 | 5-chloro-8-nitro-isoquinoline hydro-iodide |
| 63 | 5-bromo-isoquinoline |
| 64 | 5-bromo-isoquinoline hydrochloride |
| 65 | 5-iodo-isoquinoline |
| 66 | 5-cyano-isoquinoline |
| 67 | 5-cyano-isoquinolinium trifluoroacetate |
| 68 | 5-nitro-isoquinoline |
| 69 | 5-nitro-isoquinoline hydrochloride |
| 70 | 5-nitro-isoquinoline hydrobromide |
| 71 | 5-nitro-isoquinoline hydro-iodide |
| 72 | 5-nitro-isoquinolinium trifluoroacetate |
| 73 | 5-nitro-isoquinolinium monochloro-difluoroacetate |

TABLE VIII-continued

| No. | Compound |
|-----|----------|
| 74 | 5-nitro-isoquinolinium penta-fluoro-propionate acid |
| 75 | 5-nitro-isoquinolinium 2,4-dinitro-phenoxide |
| 76 | 5-nitro-isoquinolinium 2,6-dichloro-4-nitro-phenoxide |
| 77 | 5-nitro-isoquinolinium 2,6-dibromo-4-nitro-phenoxide |
| 78 | 5-nitro-isoquinolinium pentachlorophenoxide |
| 79 | 5-nitro-isoquinolinium tetrabromo-m-cresoxide |
| 80 | 5-nitro-isoquinolinium 2,4-dinitro-benzoate |
| 81 | 5-amino-isoquinoline |
| 82 | 5-amino-isoquinoline dihydrochloride |
| 83 | 5-amino-isoquinoline dihydro-iodide |

EXAMPLE 57

This example describes the pre-emergent herbicidal activity of compositions according to the present invention.

Aqueous sprays comprising 0.5% w/v of compounds No's. 5, 6, 40 and 48 were prepared according to the method of Example 56 above.

Japanese Millet seeds were sprinkled onto the surface of soil in each of five boxes and covered with a thin layer of sand. Each box was then sprayed with a quantity of one of the aqueous sprays according to the present invention providing an application rate equivalent to 5 lbs/acre of active ingredient compound, and the remaining box was sprayed with 100 ml of water for comparision purposes. The boxes were then lightly watered with an overhead spray, and placed in a glasshouse to encourage germination of the seeds. Three weeks later the boxes were removed from the glasshouse and assessed on a scale of 0 to 3 inclusive, where 0 represents substantially complete germination and 3 represents substantially complete prevention of germination. The results obtained are presented in Table IX below.

TABLE IX

| Compound No. | Pre-emergence Herbicidal Activity (rating) |
|---|---|
| 5 | 3 |
| 6 | 2 |
| 40 | 2 |
| 48 | 3 |
| Control | 0 |

EXAMPLE 58

This example describes the post-emergent herbicidal activity of compositions according to the present invention.

Aqueous sprays comprising as active ingredient compounds No's. 5, 7, 9, 23, 24, 27, 44, 45, 46, 47, 48, 68, 69, 70, 71, 72, 73, 78 and 80, and present in concentrations of 0.1% w/v, 0.5% w/v, and 1.0% w/v were prepared according to the method of Example 56 above.

Japanese Millet seeds and Ryegrass seeds were sprinkled onto soil in separate boxes, and then in each case covered with a thin layer of sand. The boxes were then lightly watered with an overhead spray, and placed in a glasshouse for one week to permit germination of the seeds and plant growth to a height of 4 to 5 inches. The boxes were then removed from the glasshouse, and each box was sprayed with one of the aqueous sprays described above. In each case the total spray volume was chosen to provide 1, 5 or 10 lbs/acre of active ingredient compound. For comparison purposes two boxes, one containing one week old Ryegrass seedlings and one containing one week old Japanese Millet seedlings, were sprayed lightly with water only. After spraying the boxes were returned to the glasshouse for a further 3 weeks and then assessed on a scale of 0 to 3 inclusive, where 0 represents substantially no damage to plant growth, and 3 represents substantially complete kill of the plants. The results are presented in Table X below:

TABLE X

| Active Ingredient Compound No. | Application Rate(lbs/acre) | Post emergent Herbicidal Activity (rating) | |
|---|---|---|---|
| | | Ryegrass | Japanese Millet |
| 5 | 10 | 3 | 3 |
|   | 5  | 1 | 2 |
| 7 | 5  | 3 | 2 |
|   | 1  | 1 | 1 |
| 9 | 10 | 1 | 3 |
|   | 5  | 1 | 3 |
| 23 | 10 | 2 | 3 |
|    | 5  | 0 | 3 |
| 24 | 10 | 3 | 3 |
|    | 5  | 1 | 3 |
| 27 | 10 | 2 | 3 |
|    | 5  | 2 | 2 |
|    | 1  | 1 | 3 |
| 44 | 10 | 3 | 3 |
|    | 5  | 0 | 3 |
| 45 | 5  | 3 | 3 |
|    | 1  | 1 | 3 |
| 46 | 10 | 3 | 3 |
|    | 5  | 0 | 3 |
| 47 | 10 | 2 | 3 |
|    | 5  | 0 | 3 |
| 48 | 10 | 3 | 3 |
|    | 5  | 1 | 3 |
| 68 | 10 | 2 | 3 |
|    | 5  | 0 | 3 |
| 69 | 10 | 3 | 3 |
|    | 5  | 1 | 3 |
| 70 | 5  | 2 | 3 |
|    | 1  | 0 | 2 |
| 71 | 10 | 3 | 3 |
|    | 5  | 1 | 3 |
| 72 | 10 | 3 | 3 |
|    | 5  | 2 | 3 |
| 73 | 5  | 2 | 3 |
|    | 1  | 0 | 2 |
| 78 | 5  | 1 | 3 |
|    | 1  | 0 | 1 |
| 80 | 10 | 2 | 3 |
|    | 5  | 0 | 1 |
| Control | — | 0 | 0 |

EXAMPLE 59

This example further describes the post-emergent herbicidal activity of compositions according to the present invention.

Aqueous sprays comprising as active ingredient compounds No's. 9, 45, 46, 47, 69, 70, 71, 72, 73, 74, 76 and 77 and present at concentrations of 0.2% w/v and 0.4% w/v were prepared according to the method of Example 56 above.

One-week-old seedlings of wheat, phalaris, wild oats, maize, sorghum, barley, lucerne, safflower, and cotton were cultivated in boxes in a glasshouse in the manner described in Example 58 hereinabove.

These one-week-old seedlings were then sprayed with each of the aqueous sprays described above, in each case the total spray volume being chosen to provide an application rate equivalent to 2 and 4 lbs per acre. In addition for comparison purposes one box of each plant species was sprayed ligthly with water. The seedlings were then returned to the glasshouse for 3 weeks, and then assessed on a scale of 0 to 5 inclusive, where 0 represents substantially no plant damage, and 5 represents substantially complete kill of plants. The results are presented in Table XI below.

were sprinkled onto soil in separate boxes, covered with sand, and lightly watered in the manner described above, and then placed in a glass house for one week to permit germination of the seeds and plant growth to a height of 4 to 5 inches. The boxes were then removed from the glass-house and each box was sprayed with one of the aqueous compositions described above in an amount providing an application rate of active ingredient compound equivalent to 1, 5 or 10 lbs per acre. After spraying the boxes were returned to the glasshouse for a further 3 weeks. The post emergence herbicidal activity of the compositions according to the present invention and described above was then assessed on

TABLE XI

| Active Ingredient Compound No. | Application Rate (lb/acre) | Wheat | Phalaris | Wild Oats | Maize | Sorghum | Barley | Lucerne | Safflower | Cotton |
|---|---|---|---|---|---|---|---|---|---|---|
| 9 | 4 | 1 | 3 | 3.5 | 1 | 3 | 3 | 4.5 | 5 | 4.5 |
|   | 2 | 0 | 0 | 0 | 0.5 | 2.5 | 1 | 3.5 | 5 | 4 |
| 45 | 4 | 4 | 5 | 5 | 4 | 0 | 4 | —* | 5 | 2 |
|   | 2 | 3 | 3 | 3 | 2 | 0 | 3 | 0 | 5 | 1 |
| 46 | 4 | 2 | 5 | 4 | 1 | 4 | 4 | 5 | 4 | 1 |
|   | 2 | 2 | 5 | 1 | 1 | 4 | 1 | 5 | 3 | 3 |
| 47 | 4 | 4 | 5 | 4 | 3 | 5 | 4 | 5 | 1 | 1 |
|   | 2 | 2 | 4 | 2 | 4 | 5 | 2 | 5 | 0 | 0 |
| 69 | 4 | 0.5 | 3 | 1 | 0 | 3 | 2.5 | 5 | 4 | 4.5 |
|   | 2 | — | — | — | — | — | — | — | — | — |
| 70 | 4 | 2.5 | 3 | 3 | 4.5 | 4.5 | 4.5 | 5 | 5 | 5 |
|   | 2 | 0 | 1 | 0 | 1.5 | 1.5 | 2.5 | 4 | 0 | 4 |
| 71 | 4 | 3 | 5 | 4 | 2 | 5 | 4 | 5 | 4 | 3 |
|   | 2 | 3 | 4 | 4 | 1 | 4 | 4 | 5 | 2 | 1 |
| 72 | 4 | 4 | 5 | 4 | 3 | 5 | 4 | 5 | 3 | 3 |
|   | 2 | 3 | 3 | 3 | 1 | 3 | 3 | 5 | 0 | 0 |
| 73 | 4 | — | — | — | — | — | — | — | — | — |
|   | 2 | 1 | 0 | 1 | 2 | 2 | 3 | 5 | 3 | 3 |
| 74 | 4 | 3 | 3.5 | 2.5 | 1.5 | 3.5 | 3 | 5 | 3.5 | 3 |
|   | 2 | 2.5 | 1 | 2 | 1.5 | 2.5 | 2.5 | 4.5 | 1 | 1.5 |
| 76 | 4 | — | — | — | — | — | — | — | — | — |
|   | 2 | 1 | 3 | 1 | 2 | 4 | 4 | 5 | 5 | 4 |
| 77 | 4 | 1 | 4 | 1 | 2 | 4.5 | 1 | 4.5 | 5 | 0 |
|   | 2 | 2.5 | 0 | 2.5 | 4.5 | 3.5 | 0 | 0 | 5 | 0 |
| Control | 0 | 0 | 0 | 0 | 0 | 0 | 0 | 0 | 0 | 0 |

*A dash "—" in the table indicates that no test was carried out at this concentration.

EXAMPLE 60

This example describes the selective pre- and post-emergence herbicidal activity of certain of the compositions according to the present invention, and comprising as active ingredient compound No. 38.

Aqueous sprayable compositions comprising compound No. 38 present in concentrations of 0.1% w/v, 0.5% w/v, and 1.0% w/v were prepared according to the method of Example 56 hereinabove.

Seeds of ipomoea, mustard, sunflower, wheat, wild oats, ryegrass, Japanese Millet and peas were sprinkled onto the surface of soil in separate boxes and covered with a thin layer of sand. Each box was then sprayed with one of the aqueous compositions described above and comprising 0.1% w/v, 0.5% w/v and 1.0% w/v of active ingredient compound, in a quantity suitable for providing an application rate equivalent to 1, 5, and 10 lbs per acre respectively. The boxes were then lightly watered with an overhead spray and placed in a glasshouse to encourage germination of the seeds. Three weeks later the boxes were removed from the glasshouse and the pre-emergence herbicidal activity of these compositions comprising compound No. 38 was assessed on a scale of 0 to 3 inclusive, where 0 denotes substantially complete germination and 3 represents substantially complete prevention of germination. The results obtained are presented in Table XII below.

In addition seeds of ipomoea, mustard, sunflower, wheat, wild oats, ryegrass, Japanese Millet, and peas a scale of 0 to 3 inclusive, where 0 denotes substantially no damage to plant growth, and 3 represents substantially complete kill of the plants. The results are presented in Table XII below.

TABLE XII

| Plant Species | Pre-emergence herbicidal activity (rating) at application rate* of:- | | | Post-emergence herbicidal activity (rating) at application rate of: | | |
|---|---|---|---|---|---|---|
|  | 10 | 5 | 1 | 10 | 5 | 1 |
| Ipomoea | 3 | 3 | 2 | 3 | 3 | 1 |
| Mustard | 3 | 3 | 1 | 3 | 3 | 2 |
| Sunflower | 3 | 3 | 1 | 3 | 3 | 0 |
| Wheat | 0 | 0 | 0 | 0 | 0 | 0 |
| Wild Oats | 0 | 0 | 0 | 0 | 0 | 0 |
| Ryegrass | 0 | 0 | 0 | 0 | 0 | 0 |
| Japanese Millet | 0 | 0 | 0 | 0 | 0 | 0 |
| Peas | 0 | 0 | 0 | 0 | 0 | 0 |

*application rate — given in lbs/acre of active ingredient compound.

These results illustrate the selective herbicidal activity of compositions according to the present invention and comprising as active ingredient compound No. 38, when applied in both the pre- and post- emergent manner. Thus these herbicidal compositions may be utilised to effectively prevent or eradicate the growth of undesired plant species such as ipomoea, mustard, and sunflower, in areas under cultivation to economically significant crops such as wheat and peas, or in areas supporting the growth of grasses useful for grazing sheep and cattle, such as ryegrass, Japanese millet, and wild oats.

EXAMPLE 61

This example describes the insecticidal acitivity of compositions according to the present invention against larvae of the species Plutella maculipennis (cabbage moth).

Aqueous sprayable compositions comprising as active ingredients compounds No's. 9, 27, 59, 63, 68, 75, 76 and 77 and present at concentrations of 0.1% w/v and 0.2% w/v were prepared according to the manner of Example 56 hereinabove.

Each of these aqueous compositions was then sprayed onto four healthy young uninfested cabbage plants. The plants were allowed to dry and then the leaves of each plant were removed and placed in a petri dish. Five Plutella maculipennis larvae were placed in each petri dish, and the petri dishes were then allowed to stand in the laboratory for 48 hours. At the end of this period the number of larvae which had died was counted, and the results were then averaged and expressed as the following mortality rating.

| Number of larvae killed (per plant) | 0 or 1 | 2 or 3 | 4 | 5 |
|---|---|---|---|---|
| Mortality Rating | 0 | 1 | 2 | 3 |

The results obtained are presented in Table XIII below:

TABLE XIII

| Active ingredient Compound No. | Insecticidal activity — Mortality Rating at concentration of active ingredient (% w/v). | |
|---|---|---|
| | 0.2 | 0.1 |
| 9 | 3 | 3 |
| 27 | 3 | 3 |
| 59 | 3 | —* |
| 63 | 3 | 0 |
| 68 | 3 | — |
| 75 | 3 | 0 |
| 76 | 3 | 3 |
| 77 | 3 | 3 |

*A dash "—" in the table indicates that no test was carried out at this concentration.

EXAMPLE 62

This example describes the acaricidal activity of compositions according to the present invention on ova of Tetranychus urticae (two spotted mite).

Aqueous sprays comprising as active ingredient compounds No's. 14, 25, 43, 47, 68, 69, 70, 71, 72, 73, 74, 76, 78 and 79 and present in concentrations of 0.1% w/v and 0.2% w/v were prepared according to the method of Example 56 above.

French bean plants with leaves cut to 1 inch square were infested with approximately 30 ova of Tetranychus urticae each. Two days after infestation any adult mites which had developed were blown off the leaves by means of a jet of air. The infested leaves of two plants per treatment were sprayed to drip point with each of the aqueous sprays described above, and 6 days after spraying the number of ova which had hatched was determined. The control of ova obtained by these tests is presented in Table XIV below as a mortality rating, on a scale of 0 to 3, where 0 represents no damage to the ova, and 3 represents complete kill.

TABLE XIV

| Active Ingredient Compound No. | Acaricidal activity — mortality rating at % w/v concentration of active ingredient. | |
|---|---|---|
| | 0.1 | 0.2 |
| 14 | 1 | 2 |
| 25 | 0 | 3 |
| 43 | 2 | 2 |
| 47 | 1 | 2 |
| 68 | 0 | 3 |
| 69 | 2 | 3 |
| 70 | —* | 2 |
| 71 | 3 | 2 |
| 72 | 2 | 3 |
| 73 | 0 | 3 |
| 74 | 2 | 3 |
| 76 | 1 | 3 |
| 78 | 1 | 3 |
| 79 | 0 | 2 |

*No test was carried out at this concentration

EXAMPLE 63

To demonstrate the acaricidal effect of compounds 9, 59, 68, 69, 71, 72, 75, 76, 77 and 78, on adult Tetranychus urticae, aqueous sprays were prepared as in Example 56 and containing 0.025% w/v, 0.05% w/v, and 0.1% w/v of active ingredient.

French bean plants with leaves cut to 1 inch squares were infested with approximately 30 adult mites of Tetranychus urticae (two spotted mite) each. Twenty-four hours after infestation the leaves of two plants per treatment were sprayed to drip point with formulations as set out in Table XV below, and 4 days after spraying the live and dead adult mites were counted. The control of mites obtained by these tests is given in Table XV as a percentage mortality.

TABLE XV

| Active Ingredient Compound No. | Acaricidal activity — percentage mortality at % w/v concentration of active ingredient | | |
|---|---|---|---|
| | 0.025 | 0.05 | 0.1 |
| 9 | 93 | 96 | 99 |
| 59 | —* | 92 | 76 |
| 68 | — | 90 | 100 |
| 69 | — | 66 | 78 |
| 71 | 84 | 96 | — |
| 72 | — | 71 | 71 |
| 75 | 48 | 89 | 100 |
| 76 | 32 | 53 | 97 |
| 77 | — | 36 | 100 |
| 78 | — | 23 | 100 |

*A dash "—" in the Table indicates that no test was carried out at this concentration.

EXAMPLE 64

This example describes the acaricidal activity of compositions according to the present invention on the larval and adult female stages of Boophilus microplus (cattle tick).

Aqueous compositions were prepared according to the method of Example 56 above, comprising the active ingredient compounds and concentrations set out in Tables XVI and XVII below.

Twenty engorged adult female cattle ticks were then treated individually by the microsyringe technique with an aqueous composition according to the present invention and selected from those set out in Table XVI below. One microdrop (freely falling) of the aqueous composition was dropped onto the neutral portion of each tick to be treated with a microsyringe having a carefully cleaned needle of 0.15 mm internal bore and 0.4 mm external diameter. After 14 days the mortality count of the adult ticks were assessed by counting the number of eggs laid by them and the percentage hatching of these eggs. The control of adult female cattle tick for each aqueous composition, assessed as a percentage mortality, is presented in Table XVI below.

In addition approximately 100 larval ticks were immersed briefly in an aqueous composition according to the present invention and selected from those set out in Table XVII below. After 48 hours the control of larval ticks were assessed as a mortality rating of 0 to 5 inclusive, as defined hereinbelow.

| Estimated percentage kill of larval cattle ticks. | 0 – 9 | 10 – 29 | 30 – 69 | 70 – 89 | 90 – 99 | 100 |
|---|---|---|---|---|---|---|
| Mortality rating | 0 | 1 | 2 | 3 | 4 | 5 |

The results are presented in Table XVII below.

TABLE XVI

| Active Ingredient Compound No. | Acaricidal activity — percentage mortality of adult ticks - 1.0% w/v of active ingredient |
|---|---|
| 2 | 100 |
| 3 | 75 |
| 4 | 100 |
| 8 | 50 |
| 12 | 70 |
| 20 | 95 |
| 22 | 80 |
| 25 | 100 |
| 30 | 100 |
| 37 | 80 |
| 43 | 100 |
| 47 | 100 |
| 57 | 30 |
| 62 | 100 |
| 68 | 50 |
| 69 | 75 |
| 70 | 85 |
| 71 | 100 |
| 72 | 95 |
| 81 | 70 |
| 82 | 85 |
| 83 | 100 |

TABLE XVII

| Active Ingredient Compound No. | Acaricidal activity - mortality of larval cattle ticks after 48 hours (rating). | |
|---|---|---|
| | - At 0.1% (w/v) of active ingredient | - At 1.0% (w/v) of active ingredient |
| 1 | 0 | 5 |
| 3 | 0 | 4 |
| 4 | 3 | 5 |
| 9 | 5 | 5 |
| 10 | 0 | 5 |
| 11 | 0 | 5 |
| 12 | 1 | 5 |
| 13 | 5 | 5 |
| 19 | 5 | 5 |
| 20 | 5 | 5 |
| 21 | 3 | 5 |
| 23 | 5 | 5 |
| 24 | 3 | 3 |
| 27 | 5 | 5 |
| 28 | 0 | 5 |
| 29 | 5 | 5 |
| 31 | 5 | 5 |
| 32 | 5 | 5 |
| 34 | 5 | 5 |
| 35 | 0 | 5 |
| 36 | 1 | 5 |
| 37 | 0 | 4 |
| 39 | 5 | 5 |
| 42 | 0 | 5 |

TABLE XVII-continued

| Active Ingredient Compound No. | Acaricidal activity - mortality of larval cattle ticks after 48 hours (rating). | |
|---|---|---|
| | - At 0.1% (w/v) of active ingredient | - At 1.0% (w/v) of active ingredient |
| 44 | 5 | 5 |
| 45 | 0 | 3 |
| 50 | 3 | 5 |
| 51 | 5 | 5 |
| 54 | 5 | 5 |
| 55 | 5 | 5 |
| 58 | 5 | 5 |
| 63 | 0 | 5 |
| 64 | 3 | 3 |
| 65 | 5 | 5 |
| 66 | 0 | 5 |
| 67 | 0 | 5 |
| 68 | 5 | 5 |
| 72 | 1 | 5 |
| 75 | 5 | 5 |
| 76 | 1 | 5 |
| 77 | 0 | 4 |
| 78 | 1 | 5 |

EXAMPLE 65

This example further describes the acaricidal activity of compositions according to the present invention against *Boophilus microplus* (cattle tick).

For each of the compounds No's. 3, 4, 5, 9, 13, 20, 38, 63 and 68, a sprayable emulsified concentrate was prepared by adding 1 g of the active ingredient compound to 5 ml of cyclohexanone, adding 1 ml of "Teric" N8 ("Teric" is a Registered Trade Mark of ICI Australia Limited, for a nonionic surfactant obtained by condensing an alkylphenol with ethylene oxide), and then making up the total volume of the mixture to 100 ml by adding water.

Nine calves, each aged between 12 and 24 months, weighing between 150 and 350 lbs, and each heavily infested with the "Yeerongpilly" strain of cattle tick, were treated in the following manner. A selected patch measuring approximately 6 inches square in the vicinity of the shoulders of each animal was lightly shaved with an electric razor. Each of the calves was then treated by spraying the patch thus prepared with a composition according to the present invention and selected from the group of emulsified concentrates prepared as described above.

After the treated patch on each calf had dried, those engorged adult female ticks close to dropping off were carefully stroked off, collected in a petri dish, and placed in an incubator for observations on egg laying and egg hatching. The mortality of the engorged adults collected in each case is prepared as a percentage mortality in Table XIX below.

The calves were then returned to a small yard for approximately 6 hours, after which period the control of the nymph and unengorged adult stages of cattle tick were assessed using the mortality rating system presented below in Table XVIII.

TABLE XVIII

MORTALITY RATING SYSTEM

| Control | Mortality Rating |
|---|---|
| 100% kill | + + + |
| Almost 100% kill but with 1 or 2 survivors | + +⊕ |
| Good (over 75%) kill | + + |
| Fair (under 75%) kill | +⊕ |
| Poor kill | + |
| Slight effect only | ⊕ |
| No effect | 0 |

The control obtained of the nymph, adult, and engorged adult stages of the "Yeerongpilly" strain of cattle tick is presented in Table XIX.

inoculated with *Alternaria solani* (early blight of tomatoes), and the tobacco plants were inoculated with *Peronospora tabacina* (blue mould of tobacco), in each

TABLE XIX

| Active Ingredient Compound No. | Concentration of Active Ingredient Compound (% w/v) | Mortality of Engorged Adults (%) | Mortality of Unengorged Adults (rating) | Mortality of Nymphs (rating) |
|---|---|---|---|---|
| 4 | 1.0 | 100 | + +⊕ | + +⊕ |
| 9 | 1.0 | 100 | + + | +⊕ |
| 19 | 1.0 | 70 | + + | + + |
| 34 | 1.0 | 50 | + + | + |
| 39 | 1.0 | —* | + + | ⊕ |
| 47 | 1.0 | 50 | + +⊕ | + +⊕ |
| 51 | 1.0 | —* | + + | + + |
| 54 | 1.0 | 40 | +⊕ | +⊕ |
| 71 | 1.0 | 44 | + +⊕ | + + |

*No test was carried out.

EXAMPLE 66

This example describes the fungicidal activity of compositions according to the present invention.

Aqueous sprayable compositions were prepared according to the method of Example 56 above, comprising the active ingredient compounds and concentrations set out in Table XX below.

In each case 200 milliliters of the aqueous composition was sprayed in a spray cabinet on to the following group of plants: a pot of 30 5 inch tall wheat plants; a pot of 30 5 inch tall oat plants; a pot of 30 5 inch tall tomato plants; and a box of nine 4 week old tobacco plants. Twenty-four hours after spraying the plants were infected in the following manner. The wheat plants were inoculated with *Erisyphe graminis* (wheat powdery mildew), the oat plants were inoculated with *Puccinia coronata* (oat rust), the tomato plants were case inoculation being effected by dusting the plants with a concentrated spore suspension of the appropriate fungus taken from infected plant material.

After inoculation the wheat was returned to the glass-house, and the oats, tomato plants, and tobacco plants were placed in a high humidity cabinet for 24 hours and then returned to the glass-house.

The wheat was assessed for disease 4 days, and the oats and tomato plants 8 days, after inoculation. The tobacco plants were returned to the humidity cabinet 6 days after inoculation for a period of 24 hours and then returned to the glass-house and assessed on the seventh day.

Each set of plants was assessed on a scale of 0 to 3 inclusive, where 0 denotes substantially no inhibition of development of disease, and 3 represents complete inhibition of development of disease. The results are presented in Table XX below.

TABLE XX

| Active Ingredient Compound Number | Fungicidal activity (rating) at 0.2% w/v and 0.05% w/v of active ingredient | | | | | | | |
|---|---|---|---|---|---|---|---|---|
| | Erisyphe graminis | | Puccinia coronata | | Alternaria solani | | Peronospora tobacina | |
| | 0.2 | 0.05 | 0.2 | 0.05 | 0.2 | 0.05 | 0.2 | 0.05 |
| 1 | —* | — | 2 | — | — | — | 2 | — |
| 6 | — | — | — | — | — | — | 3 | — |
| 8 | — | — | 3 | 0 | — | — | 3 | 0 |
| 9 | 3 | 3 | 3 | — | — | — | — | — |
| 17 | — | 2 | — | 3 | — | — | — | — |
| 18 | — | — | — | — | 3 | 3 | — | — |
| 23 | 3 | 0 | 3 | 3 | — | — | — | — |
| 24 | — | — | 3 | 0 | — | — | — | — |
| 25 | 2 | 1 | 3 | — | — | — | — | — |
| 26 | — | — | 2 | — | — | — | — | — |
| 27 | 3 | 3 | 3 | 3 | — | — | — | — |
| 28 | — | — | 3 | 0 | — | — | — | — |
| 29 | — | — | — | — | — | 2 | — | — |
| 33 | — | — | — | — | 2 | 2 | — | — |
| 34 | — | — | — | — | 3 | 0 | — | — |
| 40 | 3 | 0 | — | — | 2 | 0 | — | — |
| 43 | — | — | 3 | 3 | — | — | — | — |
| 44 | 3 | 0 | 3 | 0 | — | — | — | — |
| 45 | 3 | 0 | 3 | 0 | — | — | — | — |
| 47 | — | — | 3 | 0 | — | — | — | — |
| 48 | 2 | 0 | 3 | 0 | — | — | — | — |
| 49 | — | 2 | — | — | — | — | — | — |
| 50 | — | 3 | — | 3 | — | 3 | — | — |
| 52 | 3 | 3 | — | — | — | — | — | — |
| 59 | — | — | — | 3 | — | — | — | — |
| 60 | — | 3 | — | 3 | — | — | — | — |
| 61 | — | 2 | — | — | — | — | — | — |
| 62 | — | 2 | — | — | — | — | — | — |
| 68 | — | — | 3 | 0 | — | — | — | — |
| 69 | — | — | 3 | 0 | — | — | — | — |
| 70 | — | — | 3 | 0 | — | — | — | — |
| 71 | 3 | 0 | 3 | 0 | — | — | — | — |

TABLE XX-continued

| Active Ingredient Compound Number | Fungicidal activity (rating) at 0.2% w/v and 0.05% w/v of active ingredient | | | | | | | |
|---|---|---|---|---|---|---|---|---|
| | Erisyphe graminis | | Puccinia coronata | | Alternaria solani | | Peronospora tobacina | |
| | 0.2 | 0.05 | 0.2 | 0.05 | 0.2 | 0.05 | 0.2 | 0.05 |
| 72 | 3 | 0 | 3 | — | — | — | — | — |
| 76 | — | 2 | — | 3 | — | — | — | — |
| 77 | 3 | 3 | 3 | — | — | — | — | — |
| 78 | — | 2 | — | 3 | — | — | — | — |
| 79 | 3 | 3 | — | — | — | — | — | — |
| 81 | 3 | 0 | 2 | 0 | — | — | — | — |

*A dash "—" in the table indicates that no test was carried out at this concentration.

EXAMPLE 67

Aqueous dispersions of each of the compounds listed below in Table XXI were prepared according to the method of Example 56, and diluted with water and mixed with molten agar to give in each case weight per volume concentrations of active ingredient compound of 25 p.p.m. and 10 p.p.m. in the final product. The prepared agar mixtures were poured over microscopic slides. When the mixture had solidified on each slide, the slides were inoculated under a settling tower with spores of *Tilletia foetida* (stinking bunt of wheat). A slide containing no active ingredient was prepared in a similar manner. After incubation of the slides at 10°C for 6 days the inhibition of the spores was assessed on a scale of 0 to 3 inclusive where 0 represents substantially no inhibition, and 3 represents substantially complete inhibition of the spores. The control obtained is shown Table XXI below.

TABLE XXI

| Active Ingredient Compound No. | Concentration of active ingredient (p.p.m) | Fungicidal Activity-Inhibition of Spores (rating) |
|---|---|---|
| 4 | 25 | 2 |
| 12 | 10 | 3 |
| 13 | 25 | 3 |
| 14 | 25 | 2 |
| 15 | 25 | 2 |
| 16 | 10 | 3 |
| 17 | 10 | 3 |
| 19 | 25 | 3 |
| 20 | 25 | 3 |
| 23 | 25 | 3 |
| 25 | 25 | 2½ |
| 27 | 25 | 3 |
| | 10 | 1 |
| 29 | 25 | 3 |
| 32 | 10 | 3 |
| 33 | 25 | 3 |
| | 10 | 3 |
| 39 | 25 | 3 |
| 40 | 25 | 3 |
| | 10 | 1.5 |
| 41 | 25 | 2 |
| 44 | 25 | 2 |
| | 10 | 3 |
| 45 | 25 | 3 |
| 47 | 25 | 2 |
| 51 | 25 | 2 |
| 52 | 25 | 3 |
| 56 | 25 | 3 |
| 58 | 25 | 3 |
| | 10 | 3 |
| 59 | 25 | 3 |
| 60 | 25 | 3 |
| | 10 | 3 |
| 61 | 10 | 3 |
| 62 | 25 | 3 |
| | 10 | 3 |
| 63 | 25 | 2 |
| | 10 | 2 |
| 64 | 25 | 2 |
| 65 | 25 | 2 |
| | 10 | 2 |
| 69 | 10 | 3 |
| 70 | 25 | 3 |
| | 10 | 3 |

TABLE XXI-continued

| Active Ingredient Compound No. | Concentration of active ingredient (p.p.m) | Fungicidal Activity-Inhibition of Spores (rating) |
|---|---|---|
| 71 | 25 | 3 |
| 75 | 25 | 3 |
| 78 | 25 | 3 |
| 79 | 25 | 3 |
| | 10 | 3 |
| 81 | 25 | 3 |
| | 10 | 3 |
| 82 | 25 | 3 |
| | 10 | 3 |

EXAMPLE 68

This example describes the protective action of fungicidal compositions according to the present invention and comprising as active ingredient 4-bromo-5-nitro-isoquinoline, against *Erysiphe graminis* (wheat powdery mildew).

0.2 parts by weight of 4-bromo-5-nitro-isoquinoline was added to a solution of 0.25 parts by weight of "Lubrol" E ("Lubrol" is a registered trade mark) in 100 parts by weight of water, and the mixture was ball milled to produce a stable 0.2% w/v sprayable aqueous suspension. This suspension was then diluted with water to give sprayable compositions containing 0.0016, 0.008 and 0.04% w/v of active ingredient.

Fifty milliliters of each of these compositions was sprayed in a spray cabinet onto two 4-inch pots each containing 20 7 day old wheat plants. The plants were allowed to stand for 24 hours and were then infected with *Erysiphe graminis* by shaking infected plant material above them. The plants were then returned to a glass-house for 4 days and then assessed for disease on a scale of 0 to 5 inclusive, where 0 denotes substantially no reduction of disease compared to a control set of plants, and 5 represents complete prevention of disease.

For comparison purposes the procedure described above was substantially repeated but with the 4-bromo-5-nitro-isoquinoline replaced with a "Karathane" dispersible powder ("Karathane" is a trade mark for a proprietory fungicidal composition comprising 2-(1-methylheptyl)-4,6-dinitro-phenyl crotonate available commercially from Imperial Chemical Industries Limited).

The procedure described above for 4-bromo-5-nitro-isoquinoline was also substantially repeated but with the active ingredient isoquinoline compound omitted, to provide an untreated control set of plants, also for comparison purposes.

For each case the results are presented below in Table XXII.

TABLE XXII

| Active Ingredient Compound | Concentration of Active Ingredient Compound (% w/v) | Prevention of Erysiphe graminis (rating) |
| --- | --- | --- |
| 4-bromo-5-nitro isoquinoline | 0.0016 | 0 |
|  | 0.008 | 5 |
|  | 0.04 | 5 |
|  | 0.2 | 5 |
| "Karathane" | 0.0016 | 0 |
|  | 0.008 | 5 |
|  | 0.04 | 5 |
|  | 0.2 | 5 |
| Control |  0 | 0 |

EXAMPLE 69

This example describes the action of fungicidal compositions according to the present invention and comprising as active ingredient 4-bromo-5-nitro-isoquinoline, in eradicating *Erysiphe graminis* from wheat plants *after* infection has taken place.

Stable aqueous sprayable compositions comprising 4-bromo-5-nitro-isoquinoline as active ingredient present in concentrations of 0.0016, 0.008, 0.04, and 0.2% w/v were prepared according to the method of Example 68 hereinabove.

Seven-day-old wheat plants in 4 inch pots, also as described in Example 68 hereinabove, were infected with *Erysiphe graminis* by shaking infected plant material above them, and the disease was allowed to develop for 4 days. Two of the 4 inch pots, each containing 20 infected 11 day old wheat plants were then sprayed with 50 milliliters of each of the 4-bromo-5-nitro-isoquinoline aqueous sprays described above. The pots were then returned to a glass-house for 4 days, and then assessed for disease, on a scale of 0 to 5 inclusive, where 0 denotes substantially no control of disease, and 5 represents substantially complete eradication of disease.

For comparison purposes, stable aqueous sprays were prepared comprising "Milstem" as active ingredient present in concentrations of 0.0016, 0.008, 0.04, and 0.2% w/v ("Milstem" is a registered trade mark of Plant Protection Limited for a fungicidal composition comprising 5-n-butyl-2-ethylamino-4-hydroxy-6-methyl-pyrimidine as active ingredient). These sprays were then applied to infected 11 day old wheat plants, the plants being subsequently placed in a glass-house for 4 days and then assessed for disease as above.

Again, the procedure described above for 4-bromo-5-nitro-isoquinoline was substantially repeated but with the active ingredient isoquinoline compound omitted, to provide a control set of plants, also for comparison purposes.

For each case the results are presented below in Table XXIII.

TABLE XXIII

| Active Ingredient Compound | Concentration of Active Ingredient Compound (% w/v) | Eradication of Erysiphe graminis (rating) |
| --- | --- | --- |
| 4-bromo-5-nitro-isoquinoline | 0.0016 | 0 |
|  | 0.008 | 0 |
|  | 0.04 | 2 |
|  | 0.2 | 3 |
| "Milstem" | 0.0016 | 0 |
|  | 0.008 | 0 |
|  | 0.04 | 2 |
|  | 0.2 | 3 |
| Control | 0 | 0 |

EXAMPLE 70

This example further describes the fungicidal activity of compositions according to the present invention.

Aqueous sprayable compositions were prepared to the method of Example 56 above, comprising as active ingredient compounds No's. 9, 17, 43, 77 and 79, present in concentrations of 0.008% w/v, 0.04% w/v and 0.2% w/v.

In each case two hundred milliliters of the aqueous compositions was sprayed in a spray cabinet onto a pot of 30 5 inch tall oat plants, and 24 hours after spraying the plants were inoculated with *Puccinia coronata* (oat rust) by dusting with a concentrated spore suspension taken from infected plant material. After inoculation the oat plants were placed in a high humidity cabinet for 24 hours and then returned to the glass-house. The plants were then examined 8 days after inoculation, and assessed for disease on a scale of 0 to 5 inclusive, where 0 denotes substantially no inhibition of development of disease, and 5 represents substantially complete inhibition of development of disease. The results are presented in Table XXIV below.

TABLE XXIV

| Active Ingrediend Compound No. | Fungicidal Activity — Inhibition of spores (rating) at 1% w/v concentration of active ingredient compound | | |
| --- | --- | --- | --- |
|  | 0.2 | 0.04 | 0.008 |
| 9 | 4 | 3 | 3 |
| 17 | 5 | 5 | 3 |
| 43 | 4 | 3 | 2 |
| 77 | 5 | 5 | 5 |
| 79 | 4.5 | 4.5 | 2 |

EXAMPLE 71

Aqueous dispersions of compounds No's. 4, 12, 13, 19, 33, 40, 47, 58, 62, 69, 70 and 71, were prepared according to the method of Example 56 above, and diluted with water and mixed with molten agar to give in each case weight per volume concentrations of active ingredient compound of 0.4 p.p.m., 2 p.p.m., and 10 p.p.m., in the final product. The prepared agar mixtures were poured over microscopic slides. When the mixture had solidified on each slide, the slides were inoculated under a settling tower with spores of *Ustilago hordei* (covered smut). A slide containing no active ingredient was prepared in a similar manner. After incubation of the slides at 25°C for 24 hours the inhibition of the spores was assessed on a scale of 0 to 3 inclusive, where 0 represents substantially no inhibition and 3 represents substantially complete inhibition of the spores. The control obtained is shown in Table XXV below.

TABLE XXV

| Active Ingredient Compound No. | Fungicidal Activity — Inhibition of Spores (rating) at concentration (p.p.m.) of active ingredient compound. | | |
| --- | --- | --- | --- |
|  | 10 | 2 | 0.4 |
| 4 | 2 | 1 | 0 |
| 12 | 2 | 2 | 0 |
| 13 | 3 | 2 | 0 |
| 19 | 3 | 3 | 2 |
| 33 | 3 | 3 | 0 |
| 40 | 3 | 2 | 1 |
| 47 | 2 | 1 | 0 |
| 53 | 2 | 1 | 1 |
| 58 | 3 | 3 | 0 |
| 62 | 3 | 3 | 3 |
| 69 | 3 | 1 | 0 |
| 70 | 3 | 1 | 1 |
| 71 | 3 | 2 | 1 |

I claim:

1. A herbicidal composition comprising as active ingredient an effective ambient of 3-chloro-5-acetamidoisoquinoline and an inert carrier therefor.

2. A process of controlling or eradicating undesired vegetation, which process comprises treating areas infested with undesired vegetation with a composition according to claim 1 and providing 0.25 to 10 lb/acre of active ingredient.

3. A process for selectively controlling or eradicating undesired vegetation in areas under cultivation to grain or peas, which process comprises applying to the said areas a composition according to claim 1, said composition providing from 0.25 to 10 lb/acre of active ingredient.

* * * * *